United States Patent
Yang et al.

(10) Patent No.: US 11,358,920 B2
(45) Date of Patent: Jun. 14, 2022

(54) GLYCERIN-ONLY REACTION FOR ALLYL ALCOHOL PRODUCTION

(71) Applicant: Lyondell Chemical Technology, L.P., Houston, TX (US)

(72) Inventors: Xueyong Yang, Bellaire, TX (US); Daniel F. White, Houston, TX (US); Chelsee A. Arceneaux, Deer Park, TX (US); Pranit S. Metkar, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 17/390,014

(22) Filed: Jul. 30, 2021

(65) Prior Publication Data

US 2022/0048840 A1    Feb. 17, 2022

Related U.S. Application Data

(60) Provisional application No. 63/064,588, filed on Aug. 12, 2020.

(51) Int. Cl.
    *C07C 29/84*    (2006.01)
    *C07C 29/60*    (2006.01)
    *C07C 29/14*    (2006.01)

(52) U.S. Cl.
    CPC .............. *C07C 29/60* (2013.01); *C07C 29/14* (2013.01); *C07C 29/84* (2013.01)

(58) Field of Classification Search
    CPC .......... C07C 29/14; C07C 29/60; C07C 29/84
    See application file for complete search history.

(56) References Cited

U.S. PATENT DOCUMENTS

| 3,044,850 A | 7/1962 | Denton |
| 3,274,121 A | 9/1966 | Schneider |
| 4,215,077 A | 7/1980 | Matsumoto et al. |
| 5,444,141 A | 8/1995 | Guo |
| 10,919,024 B2 | 2/2021 | Yang et al. |
| 2018/0207618 A1 | 7/2018 | Kon et al. |

FOREIGN PATENT DOCUMENTS

WO    2017017122 A1    2/2017

OTHER PUBLICATIONS

Shiramizu et al., Deoxygenation of Biomass-Derived Feedstocks: Oxorhenium-Catalyzed Deoxydehydration of Sugars and Sugar Alcohols, Angew. Chem. Int. Ed. 2012, 51, 8082-8086.
Arceo et al., An Efficient Didehydroxylation Method for the Biomass-Derived Polyols Glycerol and Erythritol. Mechanistic Studies of a Formic Acid-Mediated Deoxygenation, Chemical Communications, 2009, 23, 3357-3359.
Yi et al., Rhenium-Catalyzed Transfer Hydrogenation and Deoxygenation of Biomass-Derived Polyols to Small and Useful Organics, ChemSusChem, 2012, 5, 1401-1404.
Lwin et al., Activation of Surface ReOx Sites on Al2O3 Catalysts for Olefin Metathesis, ACS Catalysis, 2015, 5,11, 6807-6814.
Canale et al., Deoxydehydration of Glycerol to Allyl Alcohol Catalyzed by Rhenium Derivatives, Catalysis Science & Technology, vol. 4, No. 10, Jun. 20, 2014, pp. 3697-3704, XP055243388.
The International Search Report and Written Opinion for PCT/US2021/043917 dated Nov. 15, 2021.

*Primary Examiner* — Sikarl A Witherspoon

(57) ABSTRACT

A process of producing allyl alcohol by reacting glycerin with $ReO_3$—$Al_2O_3$ in the presence of gamma-valerolactone (GVL) in a reactor is described. More specifically, a process to produce allyl alcohol, comprising the step of: a) reacting glycerin with $ReO_3$—$Al_2O_3$ in the presence of an inert solvent, GVL, in a reactor, and b) collecting the product comprising allyl alcohol.

17 Claims, 3 Drawing Sheets

GLYCERIN-ONLY REACTION FOR ALLYL ALCOHOL PRODUCTION

CROSS-REFERENCED TO RELATED APPLICATIONS

This application claims the benefit of priority to U.S. Provisional Patent Application No. 63/064,588, filed on Aug. 12, 2020, which is incorporated herein by reference in its entirely.

TECHNICAL FIELD

The disclosure relates to a process of producing allyl alcohol from glycerin by using a gamma-valerolactone/$ReO_3$—$Al_2O_3$ catalyst system. The process can also include pretreating the glycerin feedstock to remove impurities. The process can further include reaction steps to remove undesirable byproducts and recover the solvent by breaking the heavy component into light components.

BACKGROUND

Conventionally, 1,4-butanediol (BDO) is manufactured using propylene oxide (PO) as a starting material. PO is first isomerized to allyl alcohol (AA), followed by hydroformylation with $H_2$+CO to obtain 4-hydroxybutyraldehyde, which is then hydrogenated to 1,4-butanediol. See, for example, U.S. Pat. No. 4,215,077. AA is also utilized as a hydroxyl functional monomer in the polymer industry (see, for example, U.S. Pat. No. 5,444,141).

Conventionally, allyl alcohol is derived from propylene obtained by petrochemical processes. Allyl alcohol can be produced by the isomerization of propylene oxide, as described, for example, in U.S. Pat. No. 3,274,121 (slurry phase process) and U.S. Pat. No. 3,044,850 (gas-phase process). Alternatively, allyl alcohol can be made from glycerin.

The conversion of glycerin to AA has been reported, for example, by Shiramizu and Toste 2012 (Angew. Chem. Int. Ed. 2012, Vol. 51, pp. 8082-8086); Arceo, Marsden, Bergman, and Ellman 2009 (Chemical Communications, 2009, 23, 3357); Yi, Liu, and Abu-Omar 2012 (ChemSusChem, 2012, 5, 1401). The preparation of allyl alcohol has been prepared by numerous methods including from glycerin based on a two-step reaction mechanism a first step for dehydration of glycerin into acrolein and a second step for hydrogenation of acrolein into allyl alcohol; direct preparation of allyl alcohol from glycerin not through acrolein; and preparation of allyl alcohol from glycerin without the use of a catalyst. Challenges with various reported preparation methods of allyl alcohol include the need for an expensive catalyst (e.g., methyltrioxorhenium), high levels of impurities (e.g., byproducts, such as octene), and/or low allyl alcohol yield.

For example, Toste, et al. reported on the use of methyltrioxorhenium (MTO) in a reaction in which an excess (10 equivalents or more) of a secondary alcohol such as 3-octanol is utilized as the reductant as well as solvent, with reactions being carried out in a closed vessel at temperatures above 170° C. In addition to the production of 3-octanone from the oxidative dehydrogenation reaction, byproduct octene isomers are formed as the result of dehydration reactions. It has been reported that, when employing MTO as catalyst and 3-octanol as solvent, glycerin can be converted to AA with a selectivity of 90%. However, for each mole of AA produced, 1.0 mole of 3-octanol was also being converted into octene isomers. The formation of a high level of octene isomers increases the cost of making allyl alcohol using an MTO/3-octanol catalyst system.

Formic-acid mediated conversion of glycerin to allyl alcohol has been reported to have an 84% allyl alcohol yield via the formic acid treatment. The consumption of the formic acid increases the cost of making allyl alcohol using the formic-acid mediated process.

Further, glycerin feedstock has impurity such as salts, which could deactivate the catalyst. Additionally, the resulting product also contains impurities including acrolein, oligomers of lactic acid, formic acid, making it more difficult to recover the solvent.

Accordingly, a need exists for improved catalysts and methods for the production of allyl alcohol from glycerin.

SUMMARY OF THE DISCLOSURE

This disclosure relates to a process of producing allyl alcohol from glycerin by using the gamma-valerolactone/$ReO_3$—$Al_2O_3$ catalyst system to reduce the level of octane isomer. The process can also include pretreating the glycerin feedstock to remove impurities. The process can further include reaction steps to remove undesirable byproduct and recover the solvent by breaking the heavy component into light component.

In one embodiment, the process of producing allyl alcohol comprises the steps of: a) reacting glycerin with $ReO_3$—$Al_2O_3$ in the presence of an inert solvent in a reactor, and b) collecting the product comprising allyl alcohol. The glycerin-only process eliminates the need for additional reducing agent such as 3-octanol, thereby reducing the cost of production as well as eliminating the 3-octanone and octene byproducts.

A process for producing allyl alcohol, wherein the inert solvent is gamma-valerolactone (GVL). Gamma-valerolactone is a stable, nonvolatile, nontoxic compound having high boiling point (207° C.).

A process for producing allyl alcohol, wherein the reaction is further carried out in the presence of an additional inert solvent that is not GVL, for example tetraethylene glycol dimethyl ether (tetraglyme).

A process for producing allyl alcohol, wherein the molar ratio of the inert solvent to glycerin ranges from 2:1 to 1:2.

A process for producing allyl alcohol, wherein the reactor is maintained at 180-200° C. for 4 hours.

A process for producing allyl alcohol, wherein the glycerin is pretreated prior to step a). In one embodiment, the glycerin is washed with an acid. In one embodiment, the glycerin is treated with ion exchange resins to remove impurities such as sodium. In one embodiment, the ion exchange resin is in a bead form. In one embodiment, the ion exchange resin is part of an ion exchange membrane. According to the difference in acidity or alkalinity, the ion exchange resin is divided into strong acidity (e.g., sulfonic acid group-$SO_3H$ in the molecule), medium acidity (e.g., phosphoric acid group-MPO in the molecule, phosphonic acid group-$H_2PO_3$), weak acidity (e.g., the molecule contains a carboxylic acid group —COOH, etc.), strongly basic (e.g., containing quaternary ammonium-$N(CH_3)_3OH$ in the molecule), moderately basic (e.g., tetraethylenepentamine-$H(HNCH_2CH_2)_4NH_2$ in the molecule) and weak basic (e.g., m-phenylenediamine formaldehyde resin, etc.). The resins that can be used for glycerin purification include styrene strong acid type cation exchange resin, sulfonated coal resin, styrene quaternary ammonium salt strong base type exchange resin, and phenol formaldehyde weak base type resin. A styrene strong acid type cation exchange resin and a sulfonated coal resin can remove cations such as $Na^+$, $Mg^{2+}$, and $Fe^{3+}$. The styrene quaternary ammonium salt strong base type exchange resin can remove anions such as $CO^3$, $SiO$, formic acid, phenol, and fatty acid. The phenol formaldehyde weak base resin can remove strong acid ions such as $Cl^-$, $SO_3^-$, and $PO_3^-$.

In one embodiment, the glycerin is treated with ion exchange using cationic, anionic or mixed resins. For example, Amberlite 252 (Rohm and Haas Co. (Barcelona, Spain)), a macroreticular sulfonated polystyrene-divinyl-benzene resin, can be used for sodium removal from glycerin/water mixtures because of its excellent behavior in the uptake of alkali metal ions, such as K and Cs, from non-aqueous media.

In one embodiment, the glycerin is further pre-washed with water.

A process for producing allyl alcohol, wherein the product comprises a vapor component and a liquid component. In one embodiment, the process further comprises removing the vapor component from the reactor. In one embodiment, the process further comprises distilling the vapor component with a solvent.

A process for producing allyl alcohol, further comprising the step of removing the $ReO_3$—$Al_2O_3$ catalyst from the liquid component.

A process for producing allyl alcohol, further comprising separating the gamma-valerolactone from the remaining liquid component by hydrogenation and distillation.

As used herein, the term "inert solvent" refers to solvents that are stable under the reaction condition substantially without decomposition or forming undesirable byproducts.

As used herein, "gamma-valerolactone" refers to an organic compound with the following chemical structure:

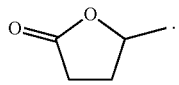

It is a colorless liquid having a boiling point of 207° C.

As used herein, "tetraethylene glycol dimethyl ether" or "tetraglyme" refers to a polar aprotic solvent with the following chemical structure:

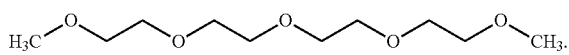

It has a boiling point of 275-276° C.

As used herein, "pretreating" of glycerin refers to the step of removing unwanted salts from the glycerin feed. The pretreating step includes acid wash, water wash, or ion exchange. The wash may be effected in one or more stages and in one or more vessel. A single vessel, such as a wash column can contain a plurality of stages.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the disclosure.

The following abbreviations are used herein:

| ABBREVIATION | TERM |
|---|---|
| AA | Allyl alcohol |
| BDO | 1,4-butanediol |
| GVL | γ-valerolactone |
| MTO | methyltrioxorhenium |
| PO | Propylene oxide |

DETAILED DESCRIPTION

Figure 1:
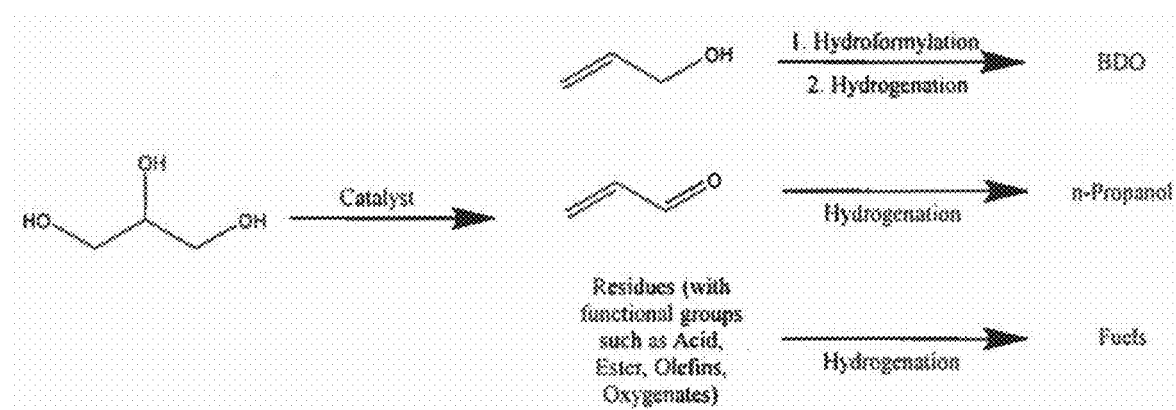
FIG. 1. presents a synthesis strategy from glycerin to allyl alcohol.

The disclosure provides a novel method of producing allyl alcohol from glycerin, particularly using $ReO_3/Al_2O_3$ catalyst system in the presence of an inert solvent to minimize octene isomers. The disclosure also describes steps of pretreating the glycerin feedstock to minimize solid residue.

Conventionally, converting glycerin to allyl alcohol typically requires an excess (10 equivalents or more) of a secondary alcohol to function as both the reductant and the solvent. The reaction is carried out in a close vessel at temperatures above 170° C. This would lead to production of 3-octanone from oxidative dehydrogenation, as well as octene isomers formed as the result of dehydration reactions. The formation of a high level of octene isomers increases the cost of making allyl alcohol using an MTO/3-octanol catalyst system.

According to this disclosure, the use of glycerin to make allyl alcohol without using 3-octanol and a catalyst reduces, or eliminates, the drawback of octene isomers formation. A heterogeneous catalyst ($ReO_3$—$Al_2O_3$) is used with an inert solvent in the reaction system while achieving the same or better allyl alcohol production.

According to this disclosure, the glycerin may be produced or derived from any suitable source, including bio-glycerin derived from bio-fuel production, non-bio-glycerin derived from conventional petrochemical processes, or obtained from commercial suppliers.

The heterogeneous catalyst $ReO_3$—$Al_2O_3$ is prepared according to Lwin et al., Activation of Surface $ReO_x$ Sites on $Al_2O_3$ Catalysts for Olefin Metathesis, *ACS Catal.* 2015, 5, 11, 6807-6814. Although known for use in metathesis, the heterogenous catalyst $ReO_3$—$Al_2O_3$ has not heretofore been used for deoxydehydration reactions such as the ones provided in the instant disclosure. The prepared heterogeneous catalysts may contain 5% to 40% of $ReO_3$ over $Al_2O_3$. The $ReO_3$—$Al_2O_3$ heterogeneous catalyst is present in the range of from 1 mole % to 13 mole %, from 7 mole % to 30 mole %, from 3 mole %, to 13 mole %, from 1 mole % to 3 mole %, from 3 mole % to 7 mole %, 7 mole % to 13 mole %, or from 13 mole % to 30 mole % of glycerin, wherein the mole ratio was calculated based on the amount of $ReO_3$ in the catalyst versus the amount of glycerin used in the reaction. The use of $ReO_3$—$Al_2O_3$ is advantageous over $ReO_3$ catalyst (as shown in the comparative examples below) because the heterogeneous catalyst system is easier to recover from the reaction mixture and can therefore be recycled to reduce the cost.

Glycerin, represented by the chemical formula $HOCH_2(CHOH)CH_2OH$, is also referred to as trihydroxypropane or glycerol. Although the purity of the glycerin converted to allyl alcohol via the herein disclosed catalyst and method does not limit the scope of this disclosure, it can be 80 wt. % or higher, 90 wt. % or higher, or 95 wt. % or higher, in embodiments, in order to reduce the production of reaction byproducts. In embodiments, the glycerin is obtained as a byproduct from the synthesis of bio-diesel via transesterification of vegetable oil and alcohol. This type of glycerin may be referred to as bio-glycerin or crude glycerin, and the produced allyl alcohol may thus be considered 'bio-allyl alcohol'. As used herein, 'bio-glycerol', 'bio-glycerin', 'crude glycerin', and 'crude glycerol' refer to glycerin obtained as a byproduct of bio-diesel production, and 'bio-allyl alcohol' refers to allyl alcohol derived from bio-glycerin. In embodiments, the glycerin converted to allyl alcohol via the herein disclosed rhenium catalyst and method comprises bio-glycerin, and the product comprises bio-allyl alcohol. In embodiments, the glycerin converted to allyl alcohol via the herein disclosed rhenium catalyst and method comprises non-bio-glycerin, and the product comprises non-bio-allyl alcohol. In embodiments, the glycerin converted to allyl alcohol via the herein disclosed rhenium catalyst and method comprises bio- and non-bioglycerin, and the product comprises bio-allyl alcohol and non-bio-allyl alcohol. In certain embodiments, at least 20, 30, 40, 50, 60, 70, 80, or 90 mole percent of the glycerin converted to allyl alcohol according to this disclosure comprises bio-glycerin. In other embodiments, at least 20, 30, 40, 50, 60, 70, 80, or 90 mole percent of the glycerin converted to allyl alcohol according to this disclosure comprises non-bio-glycerin.

The conversion of glycerin to allyl alcohol via this disclosure is a liquid phase reaction by adding the inert solvent, and the conversion conditions can comprise a reaction temperature of greater than 140° C., 150° C., 160° C., 170° C., 180° C., 190° C., or 200° C. The reaction can be carried out under ambient pressure, and the reaction temperature can be increased to the operating temperature within 30 minutes in the presence of the $ReO_2$ and/or $ReO_3$ catalyst disclosed herein.

Inert solvents can be used including tetraethylene glycoldimethyl ether (tetraglyme), γ-Valerolactone (GVL), propylene carbonate, acetophenone. It is noted that the solvents with low boiling point are susceptible to decomposition under the reaction condition. Some solvents with high boiling point may decompose, or inhibit the conversion from, glycerin to allyl alcohol. GVL is used as an inert solvent because it remains stable throughout the conversion reaction while satisfying the goal of keeping reaction products in liquid phase. However, it is expected that other inert solvents with similar properties may also be used in combination with or in place of GVL.

An allyl alcohol (AA) selectivity can be defined as:

$$\text{AA Selectivity} = (([AA]_{produced})/([Glycerin]_{feed} - [Glycerin]_{unreacted})) \times 100\% \quad (1)$$

wherein $[AA]_{produced}$ is the molar amount of produced allyl alcohol, $[Glycerin]_{feed}$ is the molar amount of glycerin in the glycerin feed to the reaction, and $[Glycerin]_{unreacted}$ is the molar amount of unreacted glycerin in the reaction product. The catalyst and method of this disclosure may provide for a selectivity to allyl alcohol that is, in certain embodiments, greater than or equal to 10%, 20%, 30%, 40%, 50%, 60%, 70%, 80%, or 90%. It is noted that in the 3-octanol-free reaction, glycerin serves not only as a reactant, but also a reducing agent. Therefore, in calculating AA selectivity, it is assumed that 50% or more of the glycerin is used as the reducing agent, and the $[Glycerin]_{feed}$ excludes the 50% glycerin.

A glycerin conversion can be defined as:

$$\text{Glycerin Conversion} = (([Glycerin]_{feed} - [Glycerin]_{unreacted})/([Glycerin]_{feed})) \times 100\% \quad (2)$$

wherein $[Glycerin]_{feed}$ is the molar amount of glycerin in the feed to the reaction, and $[Glycerin]_{unreacted}$ is the molar amount of unreacted glycerin in the reaction product. The catalyst and method of this disclosure may provide for a glycerin conversion that is, in certain embodiments, greater than or equal to 50, 60, 70, 75, or 80 mole percent, or in the range of from 50 to 100 mole percent, from 60 to 100 mole percent, from 70 to 100 mole percent, from 70 to 90 mole percent, or from 80 to 90 mole percent. It is noted that in the 3-octanol-free reaction, glycerin serves not only as a reactant, but also a reducing agent. Therefore, in calculating glycerin selectivity, it is assumed that 50% or more of the glycerin is used as the reducing agent, and the $[Glycerin]_{feed}$ excludes the 50% glycerin.

The yield of allyl alcohol (defined by the glycerin conversion multiplied by the AA selectivity) provided by the catalyst and method of this disclosure may, in embodiments, be greater than or equal to 10%, 20%, 30%, 40%, 50%, 60%, 70%, 80%, 85%, or 90%.

As noted above, the use of methyltrioxorhenium (MTO) in a reaction where 3-octanol is utilized as solvent, 3-octanone along with byproduct octene isomers form as the result of dehydration reactions. For each mole of allyl alcohol produced, one mole of 3-octanol was converted into undesirable octene isomers. The following examples were carried out to address this problem.

EXAMPLE 1

Figure 2:
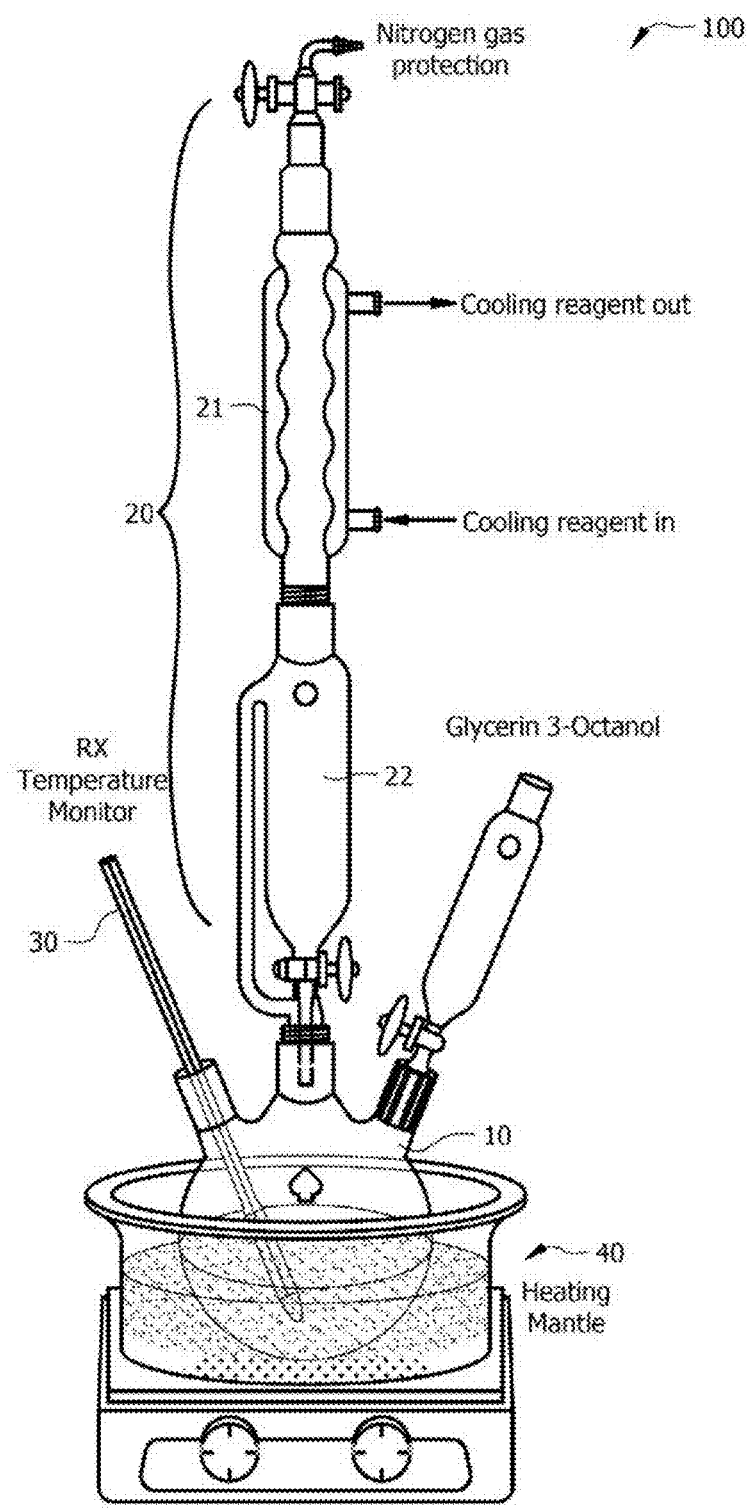
FIG. 2. provides a schematic of an experimental setup 100 in Example 1 and Comparative Examples 1-3.

FIG. 2 is a schematic of an experimental setup 100 utilized in this experiment. In a 100 mL three neck round-bottom flask 10 were placed 56.5 mmol (5.2 g) of glycerin, 49.9 mmol (5.0 g) GVL and 2.6 mmol $ReO_3$ from $ReO_3$—$Al_2O_3$ catalyst (2.0 g of 30% $ReO_3$—$Al_2O_3$). The flask 10 was connected to a distillation apparatus 20 (including thermocouple, distillation column 21 and collecting flask 22). The temperature in the reaction mixture was measured and controlled by an immersed thermocouple 30. The system was heated up to the operating temperature using a heating mantle 40. About 30 minutes later, distillation was initiated. The reaction subsequently remained at the operating temperature for an additional 3.5 hours. Once the reaction was completed and the reaction mixture cooled to room temperature, the products were drained back to reaction mixtures for Nuclear Magnetic Resonance spectroscopy (NMR) analysis. A typical NMR sample was prepared by mixing reaction products (1.5 g), 3-hydroxyl-tetrahydrofuran (0.1 g, as internal reference for NMR quantification), and dimethyl sulfoxide-d6 (1.5 g, NMR solvent). A sample for quantitative $^1$D $^{13}$C NMR experiment was collected to quantify the reaction mixture.

The results are provided in Table 1 shown below.

COMPARATIVE EXAMPLE 1-3

ReO3/3-Octanol, ReO2/3-Octanol and MTO/3-Octanol Catalyst System

The same process as in Example 1 was repeated, except the ReO$_3$—Al$_2$O$_3$ catalyst and GVL solvent were replaced with 0.66 mmol (0.143 g) ReO$_2$, 13.8 mmol (1.27 g) glycerin, 105.9 mmol (13.8 g) 3-octanol (Comp. Ex. 1), 2.7 mmol (0.63 g) of ReO$_3$, 56.4 mmol (5.2 g) glycerin, 274.0 mmol (35.7 g) 3-octanol (Comp. Ex. 2), or 1.3 mmol (0.324 g) of MTO, 25.6 mmol (2.36 g) glycerin, 367.0 mmol (47.8 g) 3-otcanol (Comp. Ex. 3).

Three catalyst systems are also provided as a comparison: one comprising rhenium dioxide; a second comprising rhenium trioxide; and a third comprising MTO/3-octanol catalyst system were utilized to convert glycerin to allyl alcohol. As solvent and reductant, 3-octanol was employed. Specifically, glycerin (obtained from SIGMA ALDRICH) was exposed to the catalyst at a temperature of 170° C. for a time period of 0.1 to 4 hours. Rhenium dioxide, rhenium trioxide, MTO, and 3-octanol were obtained from SIGMA ALDRICH.

The allyl alcohol selectivity calculated as per Equation (1), the molar percent glycerin conversion calculated as per Equation (2), and the mole ratio of octene isomers to allyl alcohol in the product comprising allyl alcohol are also shown in Table 2 below.

TABLE 1

Comparison of ReO$_3$—Al$_2$O$_3$/GVL, ReO$_2$/ReO$_3$/MTO with 3-Octanol

| Example #<br>Catalyst<br>system/solvent | Example 1<br>ReO$_3$—Al$_2$O$_3$ &<br>GVL | Comp. Ex. 1<br>ReO$_2$ & 3-<br>Octanol | Comp. Ex. 2<br>ReO$_3$ & 3-<br>Octanol | Comp. Ex. 3<br>MTO & 3-<br>Octanol |
|---|---|---|---|---|
| Solvent/Glycerin ratio | 1 | N/A | N/A | N/A |
| Catalyst (% Molar) | 4.5 | 4.8 | 4.8 | 5.1 |
| Glycerin Conversion (% Molar) | 99.7 | 70 | 86 | 100 |
| AA Selectivity (% Molar) | 54 | 82 | 70 | 90 |
| Acrolein (% Molar) | 44 | / | / | / |

As can be seen in Table 1, the glycerin-only process in Example 1 has a 99.7% conversion rate, comparable to the MTO/3-Octanol process in Comparative Example 3. Example 1 completely eliminates octene isomer and other 3-octanol-derived byproducts. It is also to be noted that the AA selectivity in Example 1 indicates at least 50% of the glycerin serves as the reducing agent in the glycerin-to-AA reaction, thereby eliminating the need for the more expensive 3-octanol as the reducing agent. The relatively low AA selectivity in Example 1 is the result of the fact that 44% of glycerin is being converted to acrolein, which can be converted to allyl alcohol through selective hydrogenation or n-propanol. Overall valuable chemical (AA+acrolein) selectivity is at about 98%. Please note that at least half of the glycerin feed is being used as reducing agent, as opposed to the three comparative examples where 3-octanol served as the reducing agent and would generate byproducts such as octene. In theory, at least 50% of glycerin is used as a reducing agent during this reaction. As a consequence, acrolein is produced from glycerin reduction. The overall economic benefit of this reaction is not using 3-octanol or other expensive secondary alcohol as a reducing agent. Additionally, the acrolein byproduct can be further converted to allyl alcohol through selective hydrogenation, thereby adding value to the process.

The GVL-glycerin ratio was varied, which plays an important role in the product distribution (allyl alcohol and acrolein), although the total yield of allyl alcohol and acrolein remained at 40 to 50 mole percent. The highest allyl alcohol selectivity of 54% was achieved when using 1/1 weight ratio of GVL/glycerin, as shown in Table 2 below. In addition, undesired by-products have three major function groups: acid/ester, alkene, and ether, which may be further converted to oxygenates through hydrogenation.

TABLE 2

Comparison between GVL/glycerin ratio

| GVL/glycerin (weight) | 3.9/1 | 2.8/1 | 1/1 | 1/2.9 |
|---|---|---|---|---|
| Glycerin conversion | 99.8% | 97.9% | 99.7% | 95.7% |
| AA selectivity | 36% | 36% | 54% | 50% |
| Acrolein selectivity | 52% | 48% | 44% | 30% |

With different GVL/glycerin ratio, the 1/1 ratio provides the highest allyl alcohol selectivity (54%) as compared to the 3.9/1 or 2.8/1 ratio (36%). Additionally, the 1/1 GVL/glycerin ratio provides almost identical glycerin conversion rate (99.7%) to the highest conversion rate when using 3.9/1 ratio (99.8%). Acrolein selectivity of the 1/1 GVL/glycerin ratio is 44%, which is lower than the 3.9/1 ratio (52%), but still in the acceptable 20+% range.

It is shown that the glycerin/GVL/ReO$_3$—Al$_2$O$_3$ system of this disclosure provides a low cost option to produce allyl alcohol and other valuable chemicals from glycerin by eliminating the need of 3-octanol (or other secondary alcohols) as reaction reductant. The glycerin/GVL/ReO$_3$—Al$_2$O$_3$ system also offers a feasible option to recycle rhenium in a commercial scale process, as discussed below.

Commercial Process of Allyl Alcohol Production from Glycerin

Figure 3:
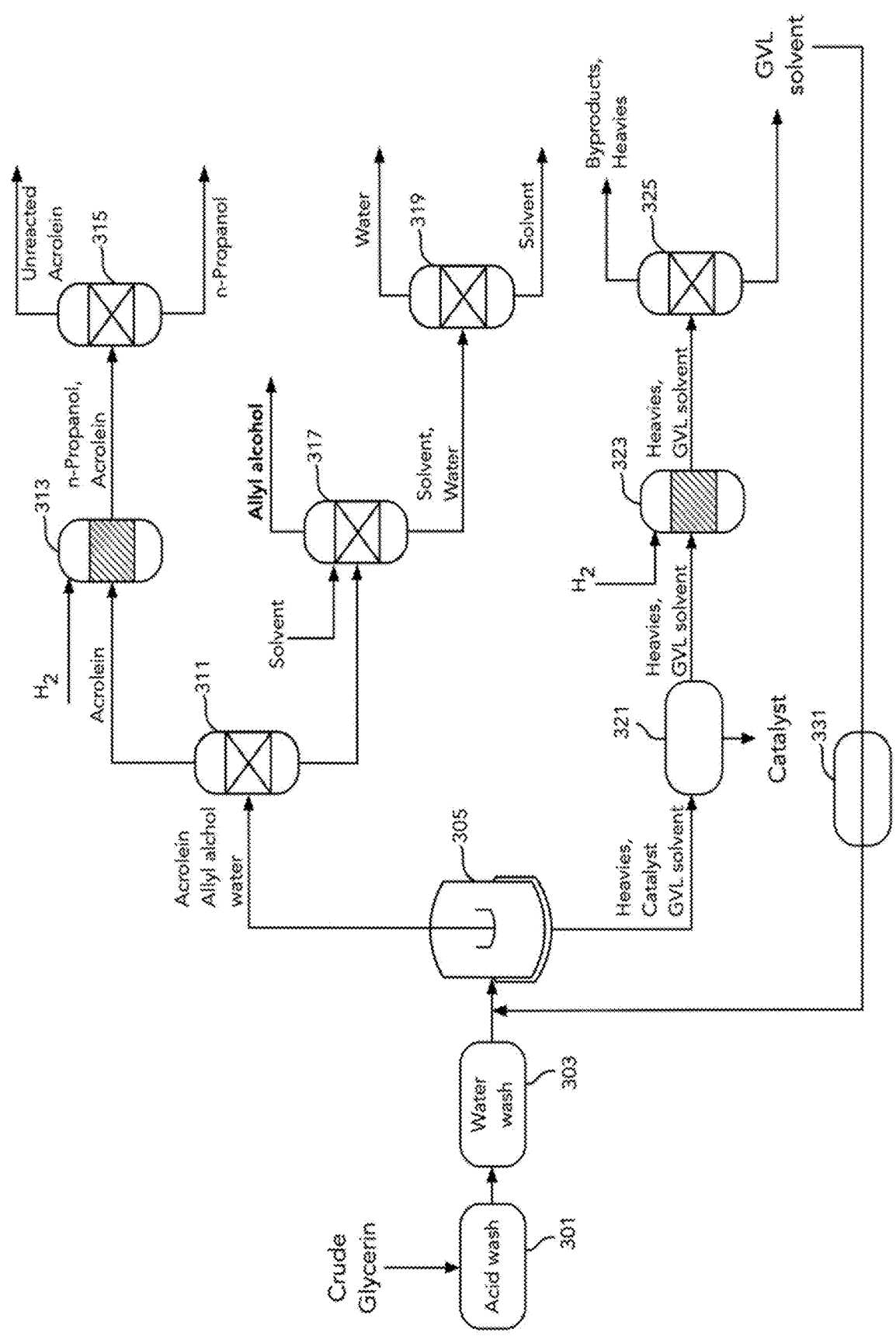
FIG. 3. provides a schematic of process flow diagram of this disclosure.

In a larger scale production of allyl alcohol, a process flow diagram is illustrated in FIG. 3. The commercial grade crude glycerin typically comprises salts that could deactivate the catalysts, especially the ReOx. Therefore, pretreating the crude glycerin to remove the salts would increasing the overall efficiency the crude glycerin feedstock first undergoes acid wash 301, followed by water wash 303. Alternatively, an ion-exchange treatment can be used to remove the salts in the crude glycerin.

The pretreated glycerin is then mixed with γ-valerolactone solvent, and the mixture is introduced into a reactor 305 with catalyst to convert into allyl alcohol and other byproducts, such as acrolein, as well as certain heavy components.

In one embodiment, the reactor is a slurry reactor where the catalyst and reactor solution are present in the form of slurry. Different reactor configuration is possible, for example, in one embodiment the reactor is a fixed bead reactive distillation unit, where the catalyst is in the form of a fixed bed, and the products are separated from the top of the column. Other reactor configurations may also be used.

The reactor 305 is configured such that allyl alcohol, acrolein, water and other low boiling point byproduct are removed from the reactor 305 in vapor form and introduced into a distillation column 311, whereas the catalyst, GVL solvent, and impurities with high boiling point (heavies) are removed from the bottom of the reactor 305.

In the distillation column 311, the lighter acrolein is removed from the top, whereas the heavier allyl alcohol and water are separated and introduced into a separate extractive distillation unit 317.

In the extractive distillation unit 317, an additional solvent can be added to break the azeotrope between allyl alcohol and water in order to recover the allyl alcohol. In one embodiment, propylene glycol can be added as the solvent, but other solvent may also be used, non-limiting examples include toluene, xylene and mixtures thereof. The feed into the extractive distillation unit 317 has temperature at 25-75° C. and pressure at 0.5-2 atm, and in the unit 317 the temperature is maintained at about 50° C. and the pressure is maintained between 0.5 and 1 atm. The unit 317 is configured to introduce the solvent at the top of the column, and the feed from the bottom of the unit in a countercurrent flow. The solvent-to-feed ratio changes the separation efficiency. In one embodiment, the solvent-to-feed ratio is maintained at 5-to-1, but other ratios may also be chosen by a person skilled in the art, depending on the conditions. For example, ratios ranging from 10/1 to 2/1 may be used. After recovering the allyl alcohol, the remaining water and added solvent can further be separated in an additional distillation column 319.

The acrolein separated from the distillation column 311 is then hydrogenated in a hydrogenation unit 313 to form n-propanol, which can be further separated from the unreacted acrolein by using an additional distillation column 315. The recovered n-propanol can be used in other processes.

The catalyst, GVL solvent and high boiling point impurities (heavies) are removed from the bottom of reactor 305 and fed into a settler 321, which separates catalyst from the remaining stream. The catalyst can therefore be recycled and optionally further reactivated.

The effluent from the settler 321 now contains the GVL solvent with the heavy impurities, and is introduced into a hydrogenation unit 323 to convert the heavy impurities into low boiling point byproducts, so that they can be separated from GVL solvent in the distillation column 325. The low boiling point byproducts can be used as fuels or lactic acid that may have other applications. The separated GVL solvent can be reintroduced to mix with further glycerin by a pump 331.

The overall process shows that the glycerin/GVL/ReO$_3$—Al$_2$O$_3$ conversion process can efficiently produce allyl alcohol with high selectivity, while also producing other valuable chemicals such as acrolein and n-propanol.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

The following references are incorporated by reference in their entirety for all purposes.

U.S. Pat. No. 3,044,850
U.S. Pat. No. 3,274,121
U.S. Pat. No. 4,215,077
U.S. Pat. No. 5,444,141
Arceo et al., Chemical Communications, 2009, 23, 3357
Lwin et al., Activation of Surface ReO$_x$ Sites on Al$_2$O$_3$ Catalysts for Olefin Metathesis, *ACS Catal.* 2015, 5, 11, 6807-6814
Shiramizu and Toste, Angew. Chem. Int. Ed. 2012, Vol. 51, pp. 8082-8086
Yi et al., ChemSusChem, 2012, 5, 1401

What is claimed is:

1. A process to produce allyl alcohol, comprising the step of:
   a) reacting glycerin with ReO$_3$—Al$_2$O$_3$ in the presence of an inert solvent in a reactor, wherein the inert solvent is gamma-valerolactone (GVL); and
   b) collecting the product comprising allyl alcohol.

2. The process of claim 1, wherein the process is free of additional reducing agent.

3. The process of claim 1, wherein the reaction is further carried out in the presence of at least two inert solvents.

4. The process of claim 3, wherein at least one of the two inert solvents is tetraethylene glycol dimethyl ether (tetraglyme).

5. The process of claim 1, wherein the molar ratio of the inert solvent to glycerin ranges from 2:1 to 1:2.

6. The process of claim 1, wherein the reactor is maintained at 180-200° C. for 4 hours.

7. The process of claim 1, further comprising pretreating the glycerin.

8. The process of claim 7, wherein the pretreating step comprises washing the glycerin with an acid or treating the glycerin with an ion exchange resin.

9. The process of claim 8, wherein the ion exchange resin is a macroreticular sulfonated polystyrene-divinylbenzene resin.

10. The process of claim 7, wherein the pretreating step further comprises washing the glycerin with water.

11. The process of claim 1, wherein the product comprises a vapor component and a liquid component.

12. The process of claim 11, further comprising removing the vapor component from the reactor.

13. The process of claim 11, further comprising distilling the vapor component with a solvent.

14. The process of claim 11, further comprising removing the ReO$_3$—Al$_2$O$_3$ from the liquid component.

15. The process of claim 14, further comprising separating the gamma-valerolactone from the remaining liquid component by hydrogenation and distillation.

16. The process of claim 1, wherein the product further comprises acrolein.

17. The process of claim 16, wherein the acrolein is separated by distillation and subsequently hydrogenated to form n-propanol.

* * * * *

UNITED STATES PATENT AND TRADEMARK OFFICE
CERTIFICATE OF CORRECTION

PATENT NO. : 11,358,920 B2
APPLICATION NO. : 17/390014
DATED : June 14, 2022
INVENTOR(S) : Yang et al.

It is certified that error appears in the above-identified patent and that said Letters Patent is hereby corrected as shown below:

In the Specification

In Column 2, Line 57, delete "group-MPO" and insert -- group-$H_2PO$ --, therefor Signed and Sealed this
Twenty-third Day of January, 2024

Katherine Kelly Vidal
*Director of the United States Patent and Trademark Office*